(12) United States Patent
Johnson

(10) Patent No.: US 7,115,097 B2
(45) Date of Patent: Oct. 3, 2006

(54) POSITIVE AIRWAY PRESSURE NOTIFICATION SYSTEM FOR TREATMENT OF BREATHING DISORDERS DURING SLEEP

(76) Inventor: Joseph L. Johnson, Brendon Park Apts., 402B Rhodora Ct., Knoxville, TN (US) 37923

( * ) Notice: Subject to any disclaimer, the term of this patent is extended or adjusted under 35 U.S.C. 154(b) by 72 days.

(21) Appl. No.: 10/681,918

(22) Filed: Oct. 9, 2003

(65) Prior Publication Data
US 2005/0076906 A1 Apr. 14, 2005

(51) Int. Cl.
  A61B 5/08 (2006.01)
  A61M 16/00 (2006.01)
(52) U.S. Cl. ............... 600/538; 600/529; 128/204.26
(58) Field of Classification Search ............ 600/529, 600/531–532, 537–541; 128/204.26, 204.27, 128/204.28, 205.25, 204.23, 204.21, 204.18
See application file for complete search history.

(56) References Cited

U.S. PATENT DOCUMENTS

| | | | |
|---|---|---|---|
| 5,203,343 A | | 4/1993 | Axe et al. |
| 5,503,146 A | * | 4/1996 | Froehlich et al. ...... 128/204.23 |
| 5,534,851 A | * | 7/1996 | Russek ............ 340/573.4 |
| 5,551,419 A | | 9/1996 | Froehlich et al. |
| 5,598,838 A | * | 2/1997 | Servidio et al. ....... 128/204.23 |
| 5,664,562 A | * | 9/1997 | Bourdon ........... 128/204.23 |
| 5,927,274 A | * | 7/1999 | Servidio et al. ....... 128/204.18 |
| 6,015,388 A | | 1/2000 | Sackner et al. |
| 6,047,203 A | | 4/2000 | Sackner et al. |
| 6,240,921 B1 | | 6/2001 | Brydon et al. |
| 6,261,238 B1 | | 7/2001 | Gavriely |
| 6,349,724 B1 | | 2/2002 | Burton et al. |
| 6,360,741 B1 | * | 3/2002 | Truschel ........... 128/202.22 |
| 6,392,555 B1 | | 5/2002 | Most, Jr. |
| 6,551,252 B1 | | 4/2003 | Sackner et al. |
| 6,626,845 B1 | * | 9/2003 | Lingo et al. ........... 600/538 |
| 6,668,828 B1 | * | 12/2003 | Figley et al. ........ 128/204.18 |
| 2001/0035185 A1 | | 11/2001 | Christopher |
| 2002/0014240 A1 | | 2/2002 | Truschel |
| 2002/0088464 A1 | | 7/2002 | Truschel |
| 2002/0165462 A1 | | 11/2002 | Westbrook et al. |
| 2003/0000522 A1 | | 1/2003 | Lynn et al. |
| 2003/0000528 A1 | | 1/2003 | Eklund et al. |
| 2003/0189492 A1 | * | 10/2003 | Harvie ............. 340/573.1 |

* cited by examiner

Primary Examiner—Robert L. Nasser
Assistant Examiner—Navin Natnithithadha
(74) Attorney, Agent, or Firm—Marcia A. Devon

(57) ABSTRACT

A notification system monitors changes in air flow channeled between a positive air pressure generator and a CPAP mask supplying positive airway pressure to a patient during treatment of sleep apnea. An air flow sensor and/or pressure sensor is positioned to monitor air flow channeled to the mask. When a sensor detects a significant change in air flow and/or air pressure, a detection signal is analyzed by a controller unit microprocessor for comparisons with a preselected operating range for air flow and/or pressure. Upon verification the air flow and/or pressure is not within the preselected range, a remote transmission is transmitted to an alarm means proximal of the patient. The alarm means directs at least one stimulus to the patient for alerting and waking the patient. The alarm stimulus includes audio and/or vibratory stimuli of sufficient intensity to alert the patient that mask adjustments are required for proper CPAP treatment.

7 Claims, 3 Drawing Sheets

POSITIVE AIRWAY PRESSURE NOTIFICATION SYSTEM FOR TREATMENT OF BREATHING DISORDERS DURING SLEEP

CROSS REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of Invention

This invention pertains to a notification system for alerting a patient to adjust a mask utilized for treatment of sleep apnea. More particularly, this invention pertains to a notification system for detecting changes in airflow and/or air pressure as indicative of mask dislodgement by a sleeping patient during treatment of obstructive sleep apnea.

2. Description of the Related Art

Patients suffering from obstructive sleep apnea and central sleep apnea are typically treated with a device generating air flow having positive airway pressure (hereinafter PA pressure) that is delivered by a hose connected to a mask positioned over the nose or over the nose and mouth of a patient suffering from sleep apnea. The PA pressure of the air flow can be delivered as continuous positive airway pressure (hereinafter CPAP), as bi-level airway pressure with increased air pressure during inspiration (hereinafter BiPAP), or as variable airway pressure delivered to the mask. Many patients have difficulty tolerating the mask fitted to the patient's face during an entire night of treatment for sleep apnea. Typically, the patient will experience a sleep arousal period or will partially awaken to move about during the night, and will return to sleep without reapplying the mask. Frequently, the mask will be remain partially or fully removed by the patient with no recollection of adjusting or removing the mask. The effectiveness of the CPAP treatment for sleep apnea is significantly disrupted after the mask is partially or fully removed by the patient during sleep or during a brief waking event. A repetitive reminder system is needed to alert the patient that the mask should be readjusted or reapplied to the patient.

Prior pressure support systems typically provide a flow sensor that detects a decrease in the rate of air exhaust attributed to tube blockage and/or mask exhaust port occlusion. The decreased rate of air exhausted from a patient's mask is compared by prior support systems with an alarm threshold for a predetermined time period in order to determine if an alarm system threshold is triggered in order to alert a care-giver. After inspection and clearing of the air tube, and/or adjustment of the fit of the mask, the care-giver is typically required to reset the alarm signal. For home treatment of sleep apnea, a care-giver may not be available for immediate receipt of the alarm signal, or the care-giver may be asleep. It is most efficient to issue an alarm directly to a patient upon mask disruption.

Other prior pressure support devices typically provide an air flow sensor and an air pressure sensor that are located at the blower end of a hose connected to provide CPAP to a nose or mouth mask. The prior devices typically detect excessive mask leaks due to mouth breathing in order to provide an electronic log of the total time the device is used by the patient, whether the patient was breathing normal, whether apnea events occurred, and whether open mouth breathing occurs during the sleep cycle. It is preferred that an alarm be issued to the sleeping patient, thereby alerting the patient that his/her mask is dislodged as soon as possible after dislodgement in order to have the mask refitted and to maximize CPAP treatment of apnea throughout the sleep cycle.

To further maximize the effectiveness of sleep apnea treatment utilizing CPAP or a similar treatment, it is preferred that an alarm system provides a rapid alert to a patient when the mask is displaced during each sleep period. Issuance of an alarm directly to the patient is preferred upon detection of an increased air flow or a decreased air pressure to the mask.

A notification system is needed for detection of each disruption of positive airway pressure channeled to a mask adapted to supply positive air flow to a patient's airway during sleep apnea treatment. It is preferred that a notification system issues an alert response to the patient when one or more sensors detect significant changes in air flow or air pressure which are indicative of the mask being displaced from the patient's face.

BRIEF SUMMARY OF THE INVENTION

According to one embodiment of the present invention, a notification system is provided for monitoring changes in air flow channeled to a patient's airway by a continuous positive airway pressure (CPAP) generator unit and CPAP mask (hereinafter, mask) utilized for treatment of sleep apnea and other breathing disorders. The notification system includes a sensor positioned within a portion of the tubing extended between the CPAP generator and the mask adapted to supply positive airway pressure to the patient. When the sensor detects a change in air flow channeled to the mask, the change being indicative of air leakage from a disrupted mask, the sensor generates a detection signal that is transmitted to a controller unit. The controller unit includes a microprocessor having means for comparing and identifying whether the detection signal is within a preselected flow rate determined by one skilled in the art such as a medical practitioner. If the microprocessor identifies a detection signal other than the preselected flow rate, it is assumed the change air flow is indicative of an improperly adjusted mask. Changes in air flow provide indications that the patient has not properly secured the mask before sleep, or has disrupted the perimeter sealing of the mask during sleep, with a resulting loss of continuous positive airway pressure delivered to the patient's airway. Upon verification that the detection signal is outside the preselected flow rate, the controller unit issues an alert signal transmitted to a transmitter means. The transmitter means transmits by remote communication, such as radio frequency signals, an alarm signal to an alarm means. The alarm means issues a stimulus of sufficient intensity to awaken the patient. The alarm means includes one or more alarms providing an audible alert signal and/or a vibratory alert signal applied to the patient in sufficient intensity to awaken the patient, thereby providing a reminder to the patient to adjust the mask.

The system further provides for detecting changes in air pressure in the air flow supplied to a mask adapted to supply positive airway pressure to a patient undergoing treatment for a sleep disorder. A sensor is provided for monitoring air pressure, with the sensor issuing a pressure detection signal that is greater or lower than a preferred range of air pressure for air flow transmitted to the mask. A controller unit receives and verifies whether the detection signal is within, or is outside of, a preselected range of air pressure. If the detection signal is outside the preselected range of air pressure, the controller unit transmits an alert signal to a transmitter means for remote transmission of an alarm signal to an alarm means. Upon receipt of the alarm signal, the alarm means issues an audible stimulus or a vibratory stimulus having sufficient intensity to awaken the patient as a reminder to the patient to adjust the mask. A method for notification of changes in air flow and/or air pressure in air flow transmitted to a patient using a CPAP generator unit and mask is also disclosed herein.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Figure 1:
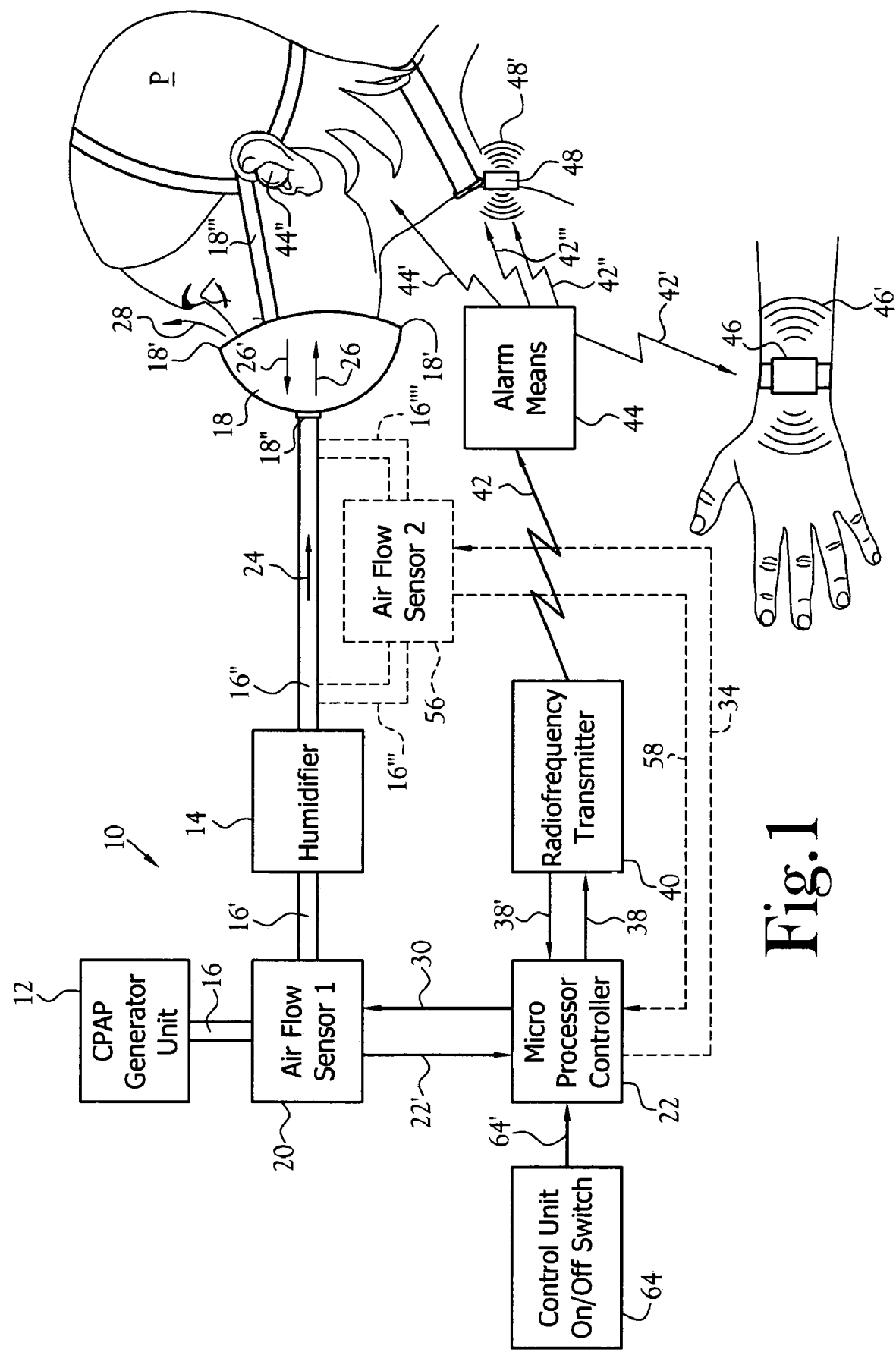
FIG. 1 is a schematic diagram of a notification system of the present invention, illustrating a continuous positive airway pressure generator and a CPAP mask, a first air flow sensor, a controller unit, a second air flow sensor, an alarm means and alarm devices for alerting the patient of a non-secured mask.
Figure 2:
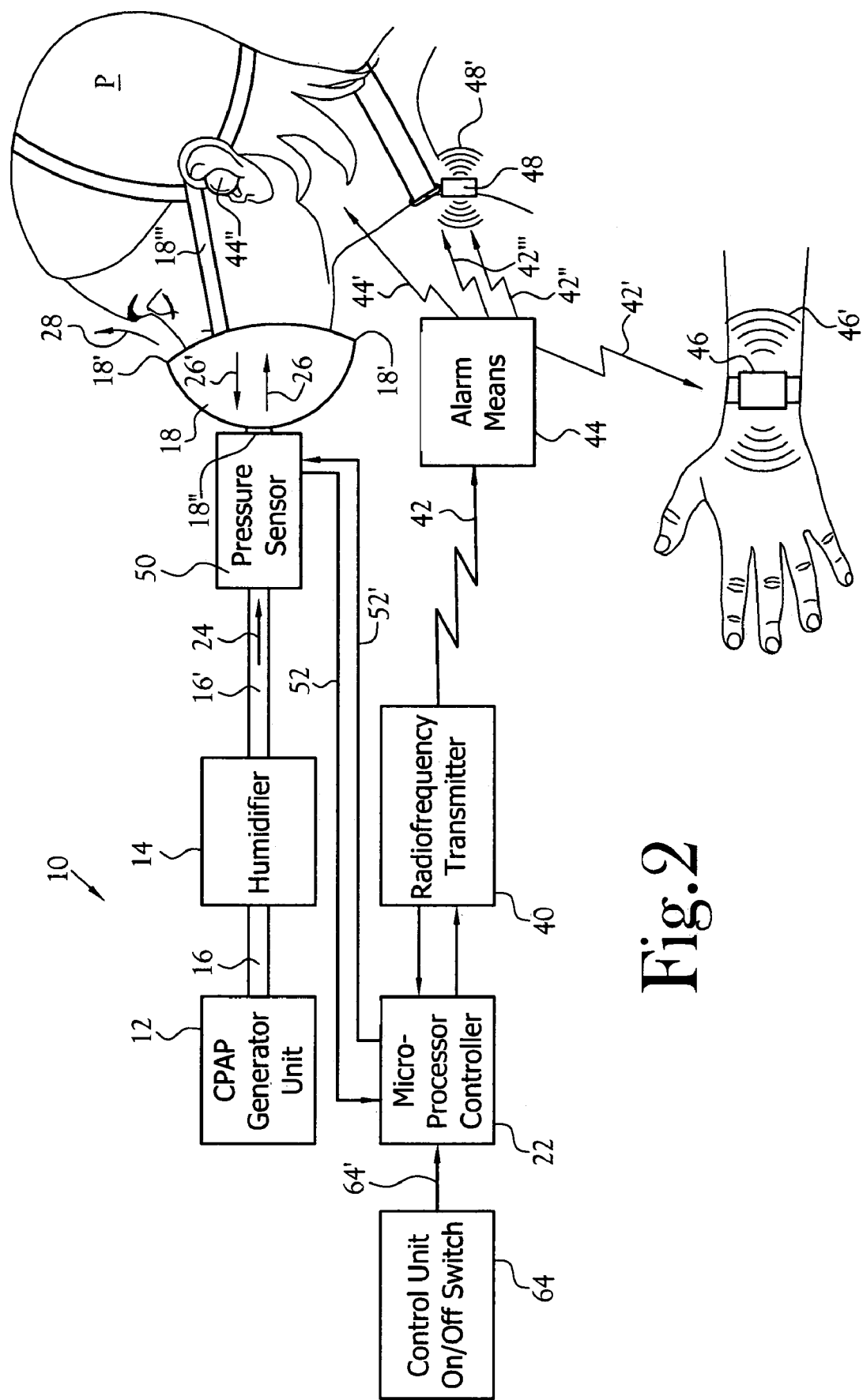
FIG. 2 is a schematic diagram of an alternative notification system illustrating a continuous positive airway pressure generator and a CPAP mask, a pressure sensor, a controller unit, an alarm means and alarm devices for alerting the patient of a non-secured mask.
Figure 3:
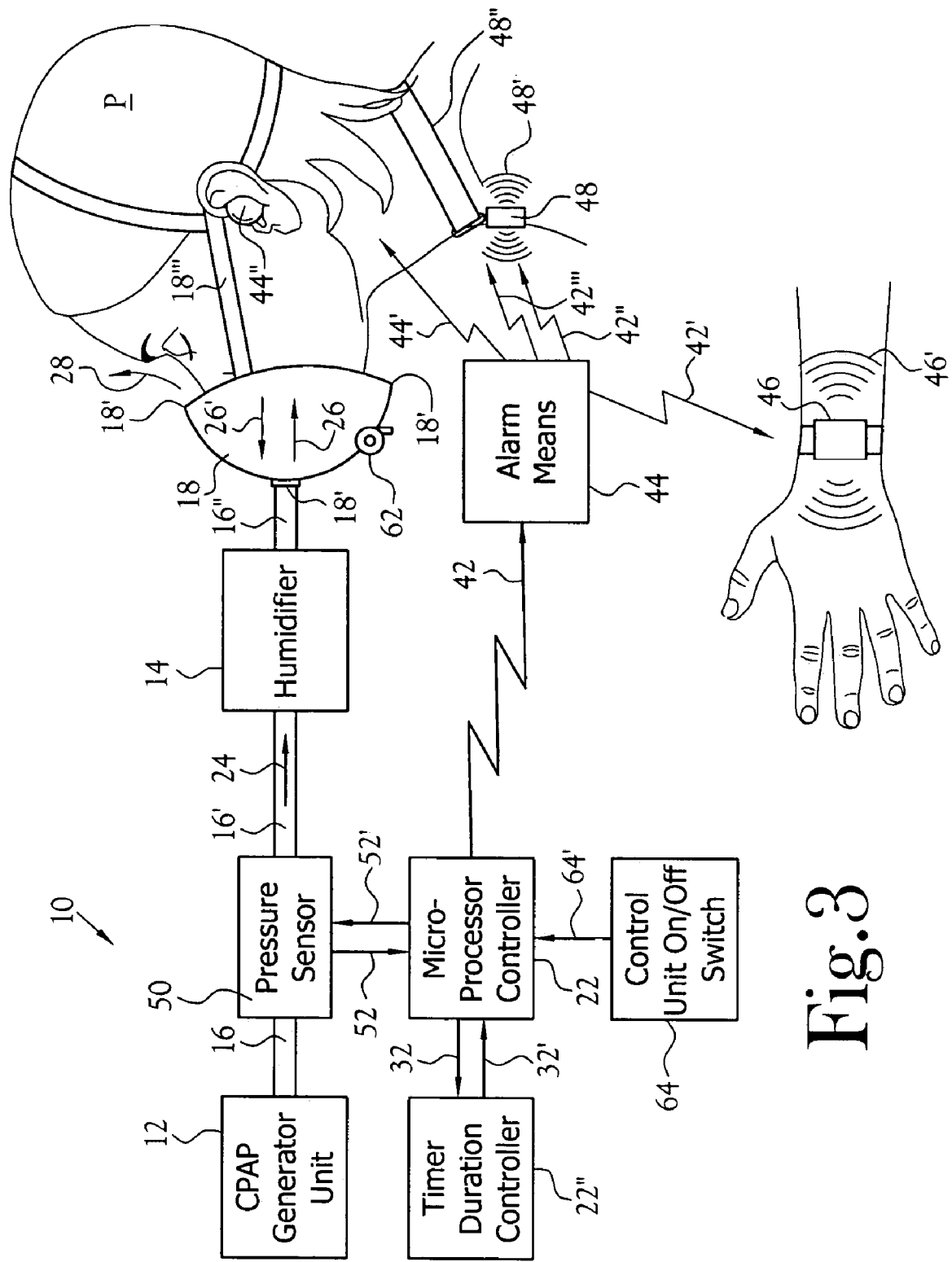
FIG. 3 is a schematic diagram of an alternative notification system illustrating a continuous positive airway pressure generator and a CPAP mask, a pressure senor, a controller unit, an alarm means and alarm devices for alerting the patient of a non-secured mask.

A notification system 10 is disclosed for monitoring changes in air flow and air pressure in a continuous positive airway pressure (CPAP) generator unit 12, humidifier unit 14, and mask 18 utilized for treatment of a breathing disorder while a patient sleeps. The breathing disorder can include obstructive sleep apnea, central sleep apnea, and related sleep disorders. In general, the notification system 10 illustrated in FIGS. 1–3 provides at least one air flow sensor 20 or a pressure sensor 50, a controller unit 22, a transmitter means 40 and an alarm means 44 for alerting the patient. Upon activation of the alarm means 44, an audio alarm device 44" and/or audio and vibration alarm devices 46, 48 issue one or more alarm signals 42'", 44', 46', 48' to the patient for notification that the mask 18 may require adjustment due to changes in air flow and/or air pressure from air leakage 28 around the mask perimeter 18'. The notification system 10 provides monitoring of changes in the air flow delivered to the mask 18, and provides a variable intensity alarm means 44 to alert a patient for maximizing duration of treatment by application of continuous positive airway pressure (CPAP) to the patient for treatment of a breathing disorder, such as sleep apnea.

In one embodiment, the notification system 10 includes a CPAP air flow generator unit 12 which generates positive air pressure channeled by air flow through flexible hoses 16, 16', 16" for delivery to a CPAP mask 18 adapted to cover the airway of a patient P. The CPAP generator unit 12 is releasably connectable by one or more hoses 16, 16', to a humidifier device 14, which is utilized to maintain a sufficient amount of moisture in the air flow delivered to the mask 18. The moisture added by the humidifier device 14 may consist of water vapor with or without medicinal vapors. Air flow is channeled to the mask 18 by one or more hoses 16', 16" which are releasably connectable at a connector valve 18" to the mask 18. Proper treatment for sleep apnea typically includes the patient P positioning the mask and maintaining the mask 18 over the patient's nose and mouth throughout the night. During treatment, positive airway pressure is maintained by channeling air flow 26 to the patient's airway and removing exhalations 26' by the patient during nocturnal sleep periods or during daytime resting periods. The effectiveness of the CPAP treatment for sleep apnea is significantly diminished if the mask 18 is partially disrupted or fully removed by the patient P during sleep or during a temporary waking event. If a patient is not alerted to disruption of the mask, or is unwilling to maintain the mask 18 over his/her nose and mouth during sleep, then treatment for sleep apnea is compromised.

Detection of significant changes in air flow and/or air pressure within the hoses 16, 16', 16" that connect to the mask 18 is accomplished by positioning an air flow sensor 20 within the air flow channeled by the hoses 16, 16', 16" to the mask 18. The sensor 20 can be positioned at a connection of first and second hoses 16, 16', at a connection of second hose 16' with the humidifier 14, at a connection to the mask 18 (see FIG. 2), at a connection between auxiliary hoses 16'" and 16"" leading to mask 18. Alternative connection locations for the air flow sensor 20 will be readily apparent to one skilled in the art, including positioning an air flow or a pressure sensor 50 proximal of a mask connector valve 18" (see FIG. 2), positioning an air flow or a pressure sensor 50 proximal of an exhaust valve 62, or positioning an air flow or a pressure sensor within a mask 18 proximal of a connector valve 18" or an exhaust valve 62. An optimal location is selected for positioning of either first air flow sensor 20, or a second air flow sensor 56, is within a path of air flow channeled to the patient's airway to accurately monitor the air flow rate during inhalation 26 and/or during exhalation 26'.

The first sensor 20 is maintained in electrical communication with a controller unit 22 which includes a microprocessor and associated electrical circuitry providing interface between the sensor 20 and the controller unit 22. The first sensor 20 includes means for monitoring air flow which is calibrated to detect air flow disruptions consisting of decreased air flow due to a blockage in the air hoses, or increased air flow due to leakage of air from the hoses or the mask 18. The first sensor 20 further includes means for generating a detection signal including an electrical circuit capable of producing a numerical value for the air flow rate detected upon each of a repetitive sampling of the air flow by the first sensor 20. Upon detection of air flow changes, the first sensor 20 issues a detection signal 22' that is transmitted by electrical means to the controller unit 22. An alternative means of transmission (not shown) is by remote transmission from first sensor 20 to the controller unit 22. Upon receipt of the detection signal 22', analysis of the significance of the detection signal 22' is provided by the microprocessor having means for comparing of one or more detection signals 22' generated by the sensor 20.

Each detection signal 22' issued by the first sensor 20 is compared utilizing an uncomplicated mathematical comparison program with one or more preselected, preferred operating parameters such as flow rate and/or air pressure, having preferred high and low boundaries for each preselected operating flow rate and/or air pressure in order to provide sufficient delivery of positive airway pressure to the patient P. One skilled in the art will be knowledgeable as to the selection of value(s) of one or more preferred operating parameters. For each detection signal 22' analyzed and verified by the microprocessor to be comparable to the preselected flow rate, or minimally higher or lower than the preselected operating range for flow rates, a feedback signal 30 is transmitted from the controller unit 22 to the first sensor 20 in order to reset the sensor 20 for continuing measuring of air flow channeled to the mask 18. A detection signal 22' issued by sensor 20 and analyzed by the microprocessor of controller unit 22 to be not within the preselected operating range is indicative of a disruption of positive air flow transmitted to the mask 18.

Upon analysis of the detection signal 22' as being outside the preselected operating range, the controller unit 22 generates one or more alert signals 38 by means for issuing such as circuitry in communication with the microprocessor. The alert signal 38 is electronically transmitted, or alternatively transmitted remotely, to a transmitter means 40 having circuitry for generation of radio frequency signals for remote delivery of the one or more alert signals 38 to an alarm means 44. If the patient P is awakened during his or her sleep cycle, and the patient will be temporarily separated from the alarm system 10, a control unit on/off and pause switch 64 is provided for manipulation by the patient P while the mask 18 is removed. The switch 64 can include a reset timer which resets the switch 64 and reactivates the controller unit 22 and air flow sensor 20 for monitoring air flow 24 in case the patient forgets to reposition the mask 18 over his or her airway upon returning to sleep.

A valid detection signal 22' indicative of a decrease in air flow or an increase an air flow is electrically transmitted to the transmitter means 40 for issuance of an alarm signal 42 transmitted by radio frequency or another frequency capable of transmission over a distance of between about one yard and up to about ten yards for receipt by the alarm means 44 positioned on the patient, or positioned proximal to the patient P. It is preferable that the alarm means 44 is not physically connected to the other units of the alarm system 10, including the delivery units of the CPAP generator 12, tubing 16, 16', 16", and the mask 18, and the sensing and analysis units including the sensor 20, the controller unit 22, and the transmitter means 40. By providing physical separation of the alarm means 44 from the sensing and analysis units, the patient P can move his or her extremities in bed without being encumbered by a connection strap or an electrical wiring chord attached to an alarm unit attached to the patient P.

The alarm means 44 includes a base unit 44 having circuitry for receiving an alarm signal 42 transmitted by radio frequency or another frequency capable of transmission from the transmitter means 40. The base unit 44 as illustrated in FIGS. 1–3 is positioned proximal to the patient and preferably attached on an extremity or near one of the patient's ear. The base unit 44 can be positioned at any of the locations illustrated in FIG. 1, including as an attachment to the mask 18, as an ear alarm 44" inserted in the patient's ear, as a wrist alarm unit 46, and/or as a neck alarm unit 48. Other locations for the base unit 44 include positioning an alarm unit to attach on the torso, leg or foot (not shown).

Upon receipt of the transmitted alarm signal 42, the alarm base unit 44, if releasably secured on the patient's torso or clothes, can issue an audible stimulus 44' of adjustable intensity and directed to alert the patient. An additional signal 42' can be directed to the releasably attachable wrist alarm unit 46, and/or a signal 42''' to a neck alarm unit 48 or another extremity, by radio frequency or another frequency capable of transmission a short distance to the alarm units 46, 48. Upon receipt of the signal from the alarm unit 44, an adjustable alarm stimulus is issued from the wrist alarm unit 46, such as an audible stimulus and/or a plurality of vibrations 46' of sufficient intensity to awaken the patient P. An alternate means for alerting the patient is for the alarm means 44, upon receipt of the alarm signal 42, to issue an adjustable alarm signal 42" directed to a releasably attached neck alarm unit 48 having means for issuing an alarm stimulus 48' such as an audible stimulus and/or a plurality of vibrations of sufficient intensity to awaken the patient P. If alarm stimulus 48' includes vibrations of neck alarm unit 48, the alarm unit 48 is adequately spaced apart from all arteries in the neck of the patient. An additional means for alerting the patient is positioning a miniaturized alarm means 44 as a removable ear unit 44" having audio means for issuance of an alert stimulus to a patient. Another embodiment includes alarm means 44 releasably attached on a patient's torso or on an extremity, and having alarm signal 42''' directed to torso or extremity unit (not shown) for issuance of an audible or vibratory stimulus.

Regardless of the positioning of the alarm means utilized for alerting the patient, the alarm means 44 issues a continuous alarm stimulus that is adjustable in intensity, and is either directly or indirectly issued by an alarm unit positioned to alert the patient to awaken and to reapply the mask 18 that has been disrupted from a proper seal against the patient's face. If an alternative mask is utilized, having a mask exhaust valve 62 (see FIG. 3), the stimulus is directed to the patient will provide a reminder for the patient to check whether the exhaust valve 62 is blocked against a pillow or clothing.

An alternative embodiment includes a second air flow sensor 56 positioned within hoses 16''', 16'''' that are utilized to provided supplemental channeling of air flow 24 to the mask 18 (see FIG. 1). The second air flow sensor 56 provides a second detection signal 58 to controller unit 22 if air flow or air pressure is measured in hoses 16''', 16'''' outside the preselected operating range for air flow and/or air pressure for delivery of positive airway pressure to the mask 18. For detection signals 58 analyzed by and verified by the microprocessor to be within the preselected, preferred air flow, or minimally higher or lower than the preselected flow rate, a feedback signal 34 is transmitted from the controller unit 22 to the second sensor 56 to reset the sensor 56 for continuing measuring of air flow rate to mask 18.

An additional embodiment includes a pressure sensor 50 positioned in the hose 16' utilized for channeling positive airway pressure into the mask 18 (see FIG. 2). The pressure sensor 50 is positioned to be exposed to the air flow 24 in order to measure decreased air pressure within hose 16', which is indicative that the mask 18 has been removed from covering the patient's airway. Increased air pressure detected by pressure sensor 50 is indicative of blockage of a mask exhaust valve 62 (see FIG. 3). Upon detecting of decreased or increased air pressure within hose 16 or 16', a pressure detection signal 52 is issued by pressure sensor 50 to controller unit 22. Each detection signal 52 is analyzed and verified by a microprocessor associated with the controller unit 22, with the microprocessor including means for analysis for analyzing the validity of each pressure detection signal 52 in relation to whether the air pressure detected is within a preselected pressure range, or minimally higher or lower than the preselected pressure range. For each detection signal 52 that is verified to be approximately similar to the preferred air pressure, a feedback signal 52' is transmitted from the controller unit 22 to the pressure sensor 50 in order to notify the sensor 50 for continuing measuring of air pressure in the air flow 24 channeled to the mask 18. A timing duration controller 22" and associated circuitry can be provided in electrical communication with the circuitry of the microprocessor and controller 22 (see. FIG. 3). The timing duration controller 22" provides timing signals 32' to the controller 22 in order to pause and/or reset the operations of the microprocessor to allow the controller 22 to operate in an hibernation mode, and not a constant operating mode, thereby providing analysis of detection signals 52 in a delayed but recurring mode of operation. The hibernation mode feature can be utilized if the generation of detection signals 52 are interrupted due to a patient's removal of the mask during extended periods of wakefulness and movement between periods of sleep. For operating modes where the controller 22 frequently receives a significant number of detection signals 52, indicative of frequent changes in the patient's breathing pattern, the controller 22 includes circuitry to provide feedback signals 32 to the timing duration controller 22" to limit its timing influence on the controller 22.

A further embodiment is illustrated in FIG. 3, including a pressure sensor 50 positioned within the air flow 24 channeled by hoses 16, 16' to the humidifier 14). If air pressure is measured in hoses 16, 16' outside the preselected operating range for air pressure for air flow to or from the mask 18, a detection signal 52 is issued by pressure sensor 50 to controller unit 22. For a detection signal 52 analyzed and verified by the microprocessor to be within the preselected operating range for air pressure, or minimally higher or lower than the preselected operating range, a feedback signal 52' is transmitted from the controller unit 22 to the pressure sensor 50 in order to reset the sensor 50 for continuing measuring of air pressure in air flow 24 channeled to humidifier 14 (see FIG. 3).

A method for notification is also disclosed, in order to alert a patient of changes in air flow channeled from a CPAP generator unit 12 to a mask adapted to supply positive airway pressure to the patient during treatment for a sleep disorder. The method for notification includes a step of monitoring air channeled to the mask 18 secured to the patient's face. The monitoring step includes positioning a sensor means 20 in the flow of air channeled to the mask 18, either positioning within any of the hoses 16, 16', 16" utilized to channel positive air flow to the patient's airway. The step of monitoring includes detecting a change in an air flow rate channeled to the mask resulting in the sensor means 20 issuing a detection signal 22' upon detection of a change in air flow rate that is not within a preselected flow rate within an operating range for air flow 26 channeled to the mask 18. The detection signal 22' is transmitted to a controller unit 22 by electrical connection, or alternatively by remote transmission.

A step of generating an alert signal 38 by the controller unit 22 occurs after receipt and analysis of the detection signal 22' by a, microprocessor associated with the controller unit 22. The step of generating includes comparing the detection signal 22' with a preselected, preferred operating range for air flow and/or air pressure as determined by one skilled in the art having training in operation of the CPAP generator unit 12 and the alarm system 10. If the detection signal 22' is within the preselected operating range, the controller unit 22 does not generate an alert signal 38, and a feedback signal 30 is transmitted by the controller unit 22 to the flow sensor 20 with the result being continued air flow monitoring. If the detection signal 22' is outside the preselected operating range, either higher or lower than the preferred range of air flow, at least one alert signal 38 is generated by the controller unit 22 and transmitted to a transmitter means 40. A verification signal 38' can be sent from the transmitter 40 to the controller 22 that an alarm signal 42 has been sent, to allow the controller 22 to reset and continue analyzing additional detection signals 22' received from the sensor 20.

In a step of transmitting, an alarm signal 42 is transmitted by radio frequency, or by another frequency capable of transmitting a sufficient distance to the patient. The alarm signal 42 is received by the alarm means 44 having a radio frequency receiver therein, which is removably positionable proximal of or preferably on the patient P. A step of alerting includes the alarm means 44 receiving the remotely transmitted alarm signal 42, with a resulting generating of an audible stimulus 44' of sufficient and adjustable intensity for directly alerting the patient.

An alternative step of alerting includes the alarm means 44 transmitting one or more alarm signals 42', 42", 42''' to a removable ear unit 44", to a removable wrist unit 46, and/or to a neck unit 48 removably attached to a necklace 48" (see FIG. 3). Upon receipt of one or more alarm signals, each respective alarm unit 44", 46, 48 generates an audible or a vibratory signal of sufficient intensity to wake the patient. If vibrations are issued by neck alarm unit 48, the vibrations are regulated in intensity and alarm unit 48 is adequately spaced apart from all neck arteries of a patient. The step of alerting includes directing an alert stimulus, either directly or indirectly by additional alarm units to the patient each time the proceeding steps of monitoring, generating, and transmitting produce an alarm signal 42 received by the alarm means 44. Therefore, if a mask 18 is adjusted by the patient but is misadjusted repeatedly during the sleep cycle, the patient is repetitively alerted by the method for notification to alert the patient to readjust the mask to maximize the effectiveness of the CPAP treatment.

Those skilled in the art will recognize that the system for monitoring a patient's use of a continuous positive air pressure unit is provided with a unique combination of components providing efficient detection of changes in air flow and/or air pressure channeled to a CPAP mask, along with timely notification to the patient, thereby alerting the sleeping patient to properly position the CPAP mask. One skilled in the art will readily understand that alternate components can be selected and utilized within the intent of the system for monitoring air way flow and/or monitoring air pressure channeled to the CPAP mask, without departing from the spirit and scope of the present invention.

From the foregoing description, it will be recognized by those skilled in the art that a notification system 10 and method for notification is provided for monitoring changes in air flow channeled from a CPAP generator unit to a CPAP mask adapted to supply positive airway pressure to a patient, and for notification of the patient when the mask is improperly adjusted in order to maximize the treatment for sleep apnea and other sleep disorders. At least one of numerous benefits of the notification system 10 and method for notification is that the elements disclosed herein for the notification system 10 and method for notification can be readily added to preexisting CPAP generator units 12, by interconnecting the air flow sensor 20 and/or a pressure sensor 50, along with the additional controller, transmitter and alarm elements 22, 40, 44, 44", 46, 48. Therefore, preexisting CPAP generator units 12 can be improved by the addition of the notification system 10 and utilization of the method for notification in order for one skilled in the art to maximize the treatment with preexisting CPAP generator units 12 for sleep apnea and other sleep disorders of a patient.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

Having thus described the aforementioned invention, I claim:

1. A system for monitoring and regulating air flow to a patient adapted to supply positive airway pressure to a patient mask during treatment of a sleep disorder, comprising:
    a CPAP generator for providing variable airway pressure;
    a first sensor for monitoring air flow channeled to the patient from said CPAP generator for generating first and second air flow rate detection signals representing the airflow to the mask and from the mask, respectively;
    a second sensor for measuring pressure in the air flow, said second sensor detecting a change in pressure at a selected place in said system, said second sensor generating a pressure detection signal upon detection of the change in pressure;
    a controller unit responsive to said first and second air flow rate detection signals said controller unit having means for interpreting, storing and comparing said first and second air flow and pressure detection signals and providing an outgoing alarm signal when the first air flow signal increases, the second air flow signal decreases and the pressure detection signal decreases;
    a remotely-controlled transmitter means in communication with said controller unit, said transmitter means generating a transmitter alarm signal in response to said outgoing alarm signal from said controller unit; and
    alarm generation means selected from the group consisting of a vibration device releasably disposed on the patient's torso, a vibration device releasably attached on the patient's extremity, an audio device movably located proximal to the patient, and a an audio device removably attachable to the patient's head.

2. The notification system of claim 1 wherein said transmitter means includes a radio frequency transmitter for transmission of said alarm signal over a sufficient distance for receipt by said alarm means having a radio frequency receiver therein.

3. The notification system of claim 1 further comprising a timing circuit in electrical communication with said controller unit microprocessor, said timing circuit provides control of a frequency of repetitive analyses accomplished by said microprocessor means for comparing, thereby providing control of the frequency of generation of said alert signal generated by said controller unit.

4. The notification system of claim 1 wherein said sensors are calibrated for detection of air pressure greater than said preselected range of air pressure.

5. The notification system of claim 1 wherein said sensor is calibrated for detection of air pressure lower than said preselected range of air pressure.

6. The system of claim 1 further including a humidifier.

7. The system of claim 1 further comprising a timing circuit in electrical communication with said controller and responsive to selection means used by the patient to indicate a hibernation mode whereby said controller disables the alarm.

\* \* \* \* \*